United States Patent
Andou et al.

(12) 
(10) Patent No.: US 6,551,801 B1
(45) Date of Patent: Apr. 22, 2003

(54) PROCESS FOR PREPARING PURIFIED DIMER OF BONE-DERIVED FACTOR

(75) Inventors: Hidetoshi Andou, Kawagoe (JP); Jun Honda, Kawagoe (JP); Sjunjiro Sugimoto, Kawagoe (JP)

(73) Assignee: Biopharm Gesellschaft zur Biotechnologischen Entwicklung von Pharmaka GmbH (DE)

( * ) Notice: Subject to any disclaimer, the term of this patent is extended or adjusted under 35 U.S.C. 154(b) by 0 days.

(21) Appl. No.: 09/331,948

(22) PCT Filed: Dec. 24, 1997

(86) PCT No.: PCT/JP97/04784
§ 371 (c)(1),
(2), (4) Date: Jul. 7, 1999

(87) PCT Pub. No.: WO98/29559
PCT Pub. Date: Jul. 9, 1998

(30) Foreign Application Priority Data

Dec. 25, 1996 (JP) .............................................. 8-355812

(51) Int. Cl.⁷ .............................. C12P 21/00; C12P 1/00; C12P 21/06; C12N 15/09; C07K 17/00
(52) U.S. Cl. ..................... 435/71.2; 435/41; 435/69.1; 435/69.4; 530/350
(58) Field of Search ........................ 435/41, 69.1, 69.4, 435/71.2; 530/350

(56) References Cited

U.S. PATENT DOCUMENTS 5,399,677 A * 3/1995 Wolfman et al. .......... 536/23.5
5,840,518 A * 11/1998 Morishita et al. .......... 435/69.1

FOREIGN PATENT DOCUMENTS

WO 96332551 10/1996

OTHER PUBLICATIONS

Chaudhuri, J. Annal. N.Y. Acad. Sci. vol. 721, pp. 374–385, May, 1994.*
Hotten et al, "Cloning . . . Factor 5", Biochem. Biophy. Res. Commun. , vol. 204, No. 2 (1994) pp. 646–652.
Yang et al, "A Genetically . . . Factor", Molecular Immunology, vol. 32, No. 12 (1995) pp. 873–881.
Werner et al, "Refolding . . . Chromatograpgy", FEBS Letters, vol. 345 (1994) pp. 125–130.

* cited by examiner

*Primary Examiner*—Yvonne Eyler
*Assistant Examiner*—Janet L. Andres
(74) *Attorney, Agent, or Firm*—Muserlian, Lucas and Mercanti

(57) ABSTRACT

A process for preparing a purified dimer of a bone-derived factor, which comprises subjecting an inclusion body of a bone-derived factor produced by genetic engineering to the following steps a) to e) in sequence:

- a) the step of treating an inclusion body of a bone-derived factor with a unfolding agent to prepare a solubilized monomer;
- b) the step of treating the solubilized monomer with a refolding solution to prepare a dimer;
- c) the step of subjecting the refolded dimer to ultrafiltration and solvent replacement;
- d) the step of subjecting the dimer solution prepared above to isoelectric precipitation; and
- e) the step of subjecting the isoelectrically precipitated dimer to reverse-phase chromatography.

6 Claims, No Drawings

PROCESS FOR PREPARING PURIFIED DIMER OF BONE-DERIVED FACTOR

This application is a 371 of PCT/JP97/04784 filed Dec. 24, 1997.

FIELD OF THE INVENTION

This invention relates to a process for the production of a purified dimeric bone morphogenetic factor. More particularly, it is concerned with a process for the production of a dimeric bone morphogenetic factor, characterizing in acquiring a purified dimeric bone morphogenetic factor from an inclusion body of a bone morphogenetic factor produced by means of a genetic engineering technology.

BACKGROUND OF THE INVENTION

A proteinaceous bone morphogenetic factor was discovered to be present in the bone matrix (Science 150, pp.893–899, 1965) and was named as "bone morphogenetic protein" (hereinafter abbreviated as BMP). Recently, cloning of plural BMP-related genes has been attempted and it has been found that all of them belong to the transforming growth factor-β (hereinafter abbreviated as TGF-β) super-family. Recombinants of some of these factors have been produced by means of a genetic engineering technology and they have been confirmed to have a bone morphogenetic activity, from which their application to the treatment of bone diseases is expected.

Of these factors, the human GDF-5 (MP52) recently discovered and belonging to the human BMP family (Biochem. Biophys. Res. Commun., 204, pp. 646–652, 1994) has been confirmed by animal tests to be effective as a bone morphogenetic factor, while it has been technically reviewed to carry forward the large-scale production thereof by expression using recombinant Escherichia coli (E. coli). However, when expressed in a large scale in E. coli and others, for instance, when the protein is produced at an amount of several grams per liter of cultured broth, the desired protein generally tends to form an inactive and insoluble inclusion body. This inclusion body is monomeric and, in order to obtain a dimer which is active as a bone morphogenetic factor, the inclusion body must be solubilized, renatured to a dimer of an original structure (the procedure generally called "refolding"), separated and purified to obtain the desired protein.

The active form of MP52 has the following or the like problems;
1) because of its low solubility in an aqueous solution, it should be handled in the presence of a denaturing agent or under acidic conditions,
2) the protein used for separation tends to nonspecifically adsorb onto a resin for liquid chromatography, and
3) the surfactant essential for refolding tends to disturb separation,
and thus it has been very difficult to establish a process for the purification thereof.

The purification process recently developed for solving the above-mentioned problems (WO 96/33215) successful in obtaining a single active form of MP52 comprises the following steps;
1. solubilizing an inclusion body by a denaturing agent,
2. separation by ion exchange chromatography,
3. sulfonation,
4. separation by gel filtration chromatography,
5. refolding,
6. recovery by isoelectric precipitation, and
7. separation by reverse-phase chromatography.

However, the above process if scaled up industrially has encountered the following and the like problems;
1) a large amount of a denaturing agent is used in order to solubilize the MP52 inclusion body, whereby modification of the protein (for example, carbamylation reaction in the case of urea) may be induced,
2) an expensive resin for chromatography, especially, for gel filtration chromatography, such as Sephacryl S-200HR or Superdex 200 pg (all available from Pharmacia Biotech) is used in a large amount,
3) a reagent used in refolding, inter alia, CHAPS and oxidized glutathione essential for dimerization reaction is extremely expensive, and
4) when isoelectric precipitation is carried out, the dilution is necessary to decrease the concentration of detergent, thus the volume of the solution is increased.

DISCLOSURE OF THE INVENTION

An object of this invention is to solve the above-mentioned problems, i.e.,
1) to use a denaturing agent in an amount as low as possible;
2) to use a chromatography resin in an amount as low as possible;
3) to replace the reagent used for refolding by other inexpensive ones and to simplify concomitant procedures with refolding,
4) to decrease the volume of the solution by removing a detergent selectively; that is, to considerably shorten the process time.

The present inventors have made feasible a simplification of the purification steps by solubilizing an inclusion body extracted from E. coli in the presence of a denaturing agent, conducting a direct refolding according to a dilution procedure and then subjecting an ultrafiltration substititing the refolding solution. This procedure appears to be similar to the first step of a process for the production of human insulin from E. coli (EP 600372A1). However, since a bone morphogenetic factor is different in properties from a soluble protein such as human insulin, it was difficult to apply the process for the production of insulin as depicted above in case of a bone morphogenetic factor. MP52 (active form) dimerized as depicted above has a low solubility and tends to adsorb onto a chromatographic resin, thus in the large-scale production, the ion exchange chromatography or hydrophobic chromatography used for human insulin or the gel filtration chromatography used in the above-mentioned WO 96/33215 could not be applied. When an ion exchanger (SP Sepharose FF, Pharmacia Biotech) is used, for example, MP52 is not completely eluted because of its strong adsorption onto the resin, even if a denaturing agent and a maximum salt concentration is used. When gel filtration (Sephacryl S-200HR, Pharmacia Biotech) is used, a strong adsorption of the protein onto a resin occurs even if a denaturing agent is used, causing an excessively broadened fractionation range and thus a very poor separation. Further, properties of the resin is altered by influence with of a surfactant such as CHAPS, which leads to loss of reproducibility. This is also applicable to the elution with an acidic solution in which MP52 is soluble. In conclusion, it is not feasible to make use of the original properties of the resin.

As explained above, it has become apparent that the purification of the desired protein in large-scale production can not be accomplished according to a general chromatographic means using aqueous system. Reverse-phase chromatography using organic solvent is the only means that could be utilized. In view of this, it was necessary to develop a purification means wherein many columns are not used. As purification means other than using columns, a fractionating method by ammonium sulfate seemed promising. However, since it had low purification efficiency and led to unnecessarily low yield, its use was cast aside. In addition, isoelectric precipitation procedure by pH adjustment was adopted, but prior to the actual procedure, an ultrafiltration procedure to remove a surfactant, CHAPS, was carried out which enabled the performance of isoelectric precipitation without increasing the volume of the solution. Conventionally, when the solution contained CHAPS, the protein solubility was high and no precipitation occurred. Therefore, a dilution was necessary to decrease the concentration of CHAPS, but a resultant extensive increase in solution volume has been a problem in process development.

This invention is directed to a process for the production of a purified dimeric bone morphogenetic factor, characterizing in subjecting an inclusion body of a bone morphogenetic factor produced by means of a genetic engineering technology to the following steps a)–e) in order, thereby producing a dimeric bone morphogenetic factor;
a) treating an inclusion body of a bone morphogenetic factor with a denaturing agent to obtain a solubilized monomer,
b) treating the solubilized monomer with a refolding solution to obtain a dimeric bone morphogenetic factor,
c) treating the dimeric bone morphogenetic factor by ultrafiltration and substitution of solvent,
d) subjecting the dimeric bone morphogenetic factor in solvent thus substituted to isoelectric precipitation, and
e) subjecting the dimeric bone morphogenetic factor thus precipitated to reverse-phase chromatography.

The inclusion body of a bone morphogenetic factor produced by means of a genetic engineering technology is preferably the one expressed in *E. coli* by means of a genetic engineering technology.

When a bone morphogenetic factor is expressed in *E. coli*, the cells are suspended in a buffer, homogenized by means of a homogenizer and centrifuged to recover an inclusion body. The inclusion body is washed with a buffer containing a detergent, for example, Triton X-100, or urea, for more than 3 times and centrifuged to obtain an inclusion body of primary purification.

The step in which an inclusion body of a bone morphogenetic factor is treated with a denaturing agent to give a solubilized monomer may be carried out by adding the inclusion body to a solution containing the denaturing agent and dissolving by stirring. For the solution containing a denaturing agent, any of those publicly known such as 8 M urea or 6 M guanidine-HCl and others in 50 mM glycine-NaOH buffer (pH 10.7) may be used.

The step in which a solubilized monomer is treated with a refolding solution to give a dimer, is carried out by diluting the protein solution obtained above with a refolding solution so as to provide a final protein concentration of 0.1 to 5.0 mg/mL, preferably 2.4 mg/mL. Although dilution has been hitherto made so as to provide a final concentration of a denaturing agent to 1M or less, it is preferable in this invention that the dilution be made so as to provide a final concentration of a denaturing agent to 1–4 M, particularly, 2.4 M, so that aggregation and precipitation of proteins may be prevented with an improved yield. For the refolding solution, any of those publicly known in the prior art such as surfactants, e.g., cholic acid or its derivatives such as 3-[(3-cholamidopropyl)dimethylammonio]-2-hydroxy-1-propanesulfonate (CHAPSO), taurocholic acid or a salt thereof, taurodeoxycholic acid or a salt thereof, and preferably, 3-[(3-cholamidopropyl)dimethylammonio]-1-propanesulfonate (CHAPS); EDTA; a combination of a reducing agent such as mercaptoethanol or dithiothreitol (DTT) with oxidized glutathione or a buffer containing cysteine or the like may be used. The advantage of using cysteine alone is that it is not necessary to use generally expensive oxidizing reagent and that it can decrease its amount of use. Therefore, it is expected to simplify the process steps and to save the cost for reagents.

The reagent contained in the refolding solution other than above described is that having a guanidino group which also prevents a protein aggregation and precipitation and increases the yield. More specifically, guanidine hydrochloride or arginine hydrochloride (Arg.HCl), preferably 0.5 M of Arg.HCl is added to the refolding solution in advance. The effect of the addition of Arg.HCl is shown in Table 1.

TABLE 1

| Protein concentration (g/L) | MP52 dimer (g/L) |
| --- | --- |
| 0.8* + 0.5 M Arg.HCl | 0.37 |
| 1.6 + 0.5 M Arg.HCl | 0.62 |
| 2.4 + 0.5 M Arg.HCl | 0.98 |
| 3.2 + 0.5 M Arg.HCl | 0.95 |
| 2.4 without Arg.HCl | protein aggregation occurred |

*Protein concentration of 0.8 g/L was the upmost limit for the protein concentration without Arg.HCl.

As shown in Table 1, without Arg.HCl, protein aggregation and precipitation occurred in the refolding solution. However, by adding Arg.HCl, the amount of protein that can be treated per refolding solution without aggregation can be increased by 2.7 fold (i.e. 0.98 g/L as opposed to 0.37 g/L). As for a buffer, those buffers using phosphate or Tris-HCl may be used, but an Arg-NaOH buffer of pH 8–10, particularly pH 8.9, is preferred.

The ultrafiltration step in which the refolded dimer is concentrated, is carried out by using a molecular weight cut-off membrane filter of 10,000 such as PSU 10K (Sartorius) and the CHAPS concentration is lowered by substituting with an acid solution, such as 0.2% phosphoric acid solution.

The step in which the solution of the dimer substituted is isoelectrically precipitated, is carried out by adding alkali solution such as NaOH to the dimer solution adjusting pH value to 7.4 to selectively precipitate a bone morphogenetic factor. After the pH adjustment, the solution is allowed to stand for one hour or more, centrifuged or filtered to remove the supernatant and the precipitate is dissolved in an acid solution such as 50 mM citric acid, 0.2% phosphoric acid or 0.05% trifluoroacetic acid solution.

The step in which the isoelectrically precipitated dimer is subjected to reverse-phase chromatography, is carried out by subjecting the acidic solution obtained above to high-performance liquid chromatography and eluting with 0–50% gradients of organic solvent such as isopropanol, acetonitrile or ethanol to recover the fractions of a dimeric bone morphogenetic factor. As resin for high-performance liquid chromatography, a polymeric resin such as SOURCE 15 RPC (6 cmφ×20 cm, manufactured by Pharmacia Biotech) is used.

The bone morphogenetic factor to be used in this invention is preferably a bone morphogenetic factor having a single molecular weight selected from the group consisting of MP52, BMP-2, BMP-4, BMP-6 and BMP-7. As an example, the *E. coli* strain having introduced therein cDNA encoding a human MP52 precursor (specifically, the *E. coli* having introduced therein a plasmid ligated with a codon encoding methionine at the 5-primer terminus in MP52- sequence of 119 residues of which the N-terminal alanine of mature human MP52 is deleted) is incubated to produce mature monomeric MP52 as inclusion body in large amounts and using the present process, mature MP52 is obtained with high purity from this inclusion body.

EXAMPLE

This invention will be more specifically explained hereinbelow by way of examples, which are not construed to limit the invention. The procedures from (2) to (4) were carried out in a low temperature chamber at 4° C., considering stability of the protein. Each step will be fully explained below.

(1) Fermentation of Human MP52 and Primary Purification of Inclusion Body

The MP52-producing *E. coli* obtained in the same manner as described in Example 2 of WO 96/33215 was precultivated in a modified SOC medium and then the precultivated broth was inoculated into 100 L of production medium. For induction, 1 mM isopropyl-β-D-thiogalactopyranoside (IPTG) was added at an early logarithmic growth phase and fermentation was continued at 32° C. until $OD_{550}$=150. After that, cells were harvested, cells were suspended in a buffer containing 25 mM Tris-HCl (pH 7.3) and 10 mM EDTA-4Na, homogenized by means of a homogenizer (manufactured by Manton Gaulin) and centrifuged to recover an inclusion body. The inclusion body was washed with a buffer containing 1 M urea as a detergent and centrifuged to obtain an inclusion body with primary purification applied.

(2) Solubilization of Inclusion Body and Refolding

One hundred g (wet weight) of the inclusion body obtained above was solubilized by stirring in 300 mL of 50 mM glycine-NaOH buffer containing 8 M urea and 5 mM ethylenediamine-tetraacetate (pH 8.9) (protein concentration being about 18 mg/mL). Refolding was performed by diluting the inclusion body solution with a refolding buffer [0.5 M Arg-NaOH (pH 8.9), 4.8 mM cysteine hydrochloride monohydrate, 0.5 M sodium chloride, 20 mM CHAPS] to 6.7 times volume (protein concentrationbeingabout 2.4 mg/mL). The mixture as such was allowed to stand at 4° C. for about 20 hours.

(3) Purification of MP52 after Refolding (Ultrafiltration)

MP52 after completion of the refolding reaction was concentrated 5 fold by using a membrane filter of 10,000 cut-off molecular weight (PSU 10K, Sartorius) and the solution was diluted and substituted by 5 fold volume with 0.2% phosphoric acid solution. By repeating the procedure three times, the CHAPS concentration is diluted theoretically by 100 fold or more.

(4) Purification of MP52 after Refolding (Isoelectric Precipitation)

Isoelectric precipitation was performed by adding NaOH solution to the substituted refolding solution adjusting the pH value to 7.4. The solution became cloudy, and then it was allowed to stand for one hour or more. Then it was centrifuged (10,000 g×15 min) and the precipitate was recovered. The precipitate was dissolved in 0.2% phosphoric acid solution.

(5) Purification of MP52 after Refolding (Reverse-Phase Chromatography)

MP52 dissolved in the phosphoric acid solution was separated by means of reverse-phase chromatography. A high-performance liquid chromatographic system using SOURCE 15 RPC (6 cmφ×20 cm, Pharmacia Biotech) as resin was operated and eluted with 0–50% ethanol gradient to recover the fractions containing dimeric MP52.

According to the above-mentioned purification process, we have succeeded in recovering an active form of MP52 in high yield as shown in Table 2. An amount of MP52 in the purification step was determined by quantification of scanned CBB-stained-electrophoresis gel image.

TABLE 2

| Step | Amount of MP52 (g) | Yield (%) |
|---|---|---|
| Solubilization | 5.4 | 100 |
| Refolding | 2.2 | 41 |
| Ultrafiltration | 1.6 | 30 |
| Isoelectric precipitation | 1.5 | 29 |
| Reverse-phase chromatography | 1.1 | 21 |

One of the advantages of the purification process in this invention is an effective reduction of the purification cost. According to a preliminary calculation, the total process cost may be reduced to about ½ per protein as compared with those in WO 96/33215. Therefore, the present purification process can be very useful in industrialization.

According to the present process, a dimeric bone morphogenetic factor having a single molecular weight can be efficiently produced in a large amount and more inexpensively, as compared with the prior art process.

We claim:

1. A process for the production of a purified dimeric bone morphogenetic factor which comprises subjecting an inclusion body of a bone morphogenetic factor to the following steps a)–c) in order, thereby producing the dimeric bone morphogenetic factor;

a) introducing a polynucleotide encoding a bone morphogenetic factor into *E. coli* expressing said bone morphogenetic factor in the form of an inclusion body in *E. coli*, recovering (and washing) said inclusion body and treating it with a denaturing agent to obtain a solubilized monomer, b) treating the solubilized monomer without purification directly with a refolding solution in a final protein concentration from 1.6 mg/ml up to 5 mg/ml to obtain a dimeric bone morphogenetic factor, c) subjecting the dimeric bone morphogenetic factor to purification.

2. The process of claim 1, wherein the refolding solution has a final concentration of said denaturing agent of 1 M–4 M.

3. The process for the production according to claim 1, wherein said refolding solution is a buffer comprising cysteine or salt thereof, sodium chloride at a concentration of 0.1 to 1.5 M, and cholic acid or its derivatives at a concentration of 5 to 100 mM and a pH in the range of 8–10.

4. The process for the production according to claim 3, wherein said refolding solution is further comprising a guanidine or arginine or a salt thereof.

5. The process for the production according to claim 1, wherein said bone morphogenetic factor is a bone morphogenetic factor selected from the group consisting of MP52, BMP-2, BMP-4, BMP-6 and BMP-7.

6. The process of claim 1 wherein the dimeric bone morphogenetic factor is purified by ultrafiltration, isoelectric precipitation and reverse-phase chromatography.

* * * * *